United States Patent
Gaik et al.

(10) Patent No.: US 11,446,293 B2
(45) Date of Patent: *Sep. 20, 2022

(54) EXTENDED RELEASE, ABUSE DETERRENT DOSAGE FORMS

(71) Applicant: SPECGX LLC, Webster Groves, MO (US)

(72) Inventors: Jonathan Gaik, Hazelwood, MO (US); Jaehan Park, Hazelwood, MO (US); Ryan Lathrop, Hazelwood, MO (US); Gary Nichols, Hazelwood, MO (US); John Schallom, Hazelwood, MO (US)

(73) Assignee: SpecGX LLC, Webster Groves, MO (US)

( * ) Notice: Subject to any disclaimer, the term of this patent is extended or adjusted under 35 U.S.C. 154(b) by 162 days.

This patent is subject to a terminal disclaimer.

(21) Appl. No.: 16/818,528

(22) Filed: Mar. 13, 2020

(65) Prior Publication Data

US 2020/0268747 A1 Aug. 27, 2020

Related U.S. Application Data

(63) Continuation of application No. 15/464,865, filed on Mar. 21, 2017, now Pat. No. 10,624,888.

(60) Provisional application No. 62/315,952, filed on Mar. 31, 2016.

(51) Int. Cl.
*A61K 31/485* (2006.01)
*A61K 9/00* (2006.01)
*A61K 9/16* (2006.01)
*A61K 9/20* (2006.01)
*A61K 9/48* (2006.01)

(52) U.S. Cl.
CPC .......... *A61K 31/485* (2013.01); *A61K 9/0053* (2013.01); *A61K 9/1617* (2013.01); *A61K 9/1635* (2013.01); *A61K 9/1641* (2013.01); *A61K 9/20* (2013.01); *A61K 9/48* (2013.01)

(58) Field of Classification Search
None
See application file for complete search history.

(56) References Cited

U.S. PATENT DOCUMENTS

| | | | |
|---|---|---|---|
| 10,624,888 B2 * | 4/2020 | Gaik | A61K 31/485 |
| 2003/0125347 A1 * | 7/2003 | Anderson | A61P 25/04 |
| | | | 514/282 |
| 2007/0190142 A1 * | 8/2007 | Breitenbach | A61P 25/36 |
| | | | 424/469 |
| 2010/0179159 A1 | 7/2010 | Alles et al. | |
| 2014/0296277 A1 | 10/2014 | Brögmann et al. | |
| 2015/0017250 A1 | 1/2015 | Wening et al. | |

FOREIGN PATENT DOCUMENTS

WO  WO-2005079760 A1 * 9/2005 ........... A61K 9/0053

OTHER PUBLICATIONS

Office Action in related European Application No. 17776311.7 dated Mar. 11, 2022, 2 pages.

* cited by examiner

*Primary Examiner* — Aradhana Sasan

(57) ABSTRACT

Extended release, abuse deterrent dosage forms comprising crush-resistant controlled-release particles that provide abuse deterrent properties to the dosage forms. The crush-resistant controlled-release particles, which comprise plastic/elastic polymers and at least one active pharmaceutical ingredient (API) or a pharmaceutically acceptable salt thereof, are prepared by a hot melt extrusion process.

20 Claims, 1 Drawing Sheet

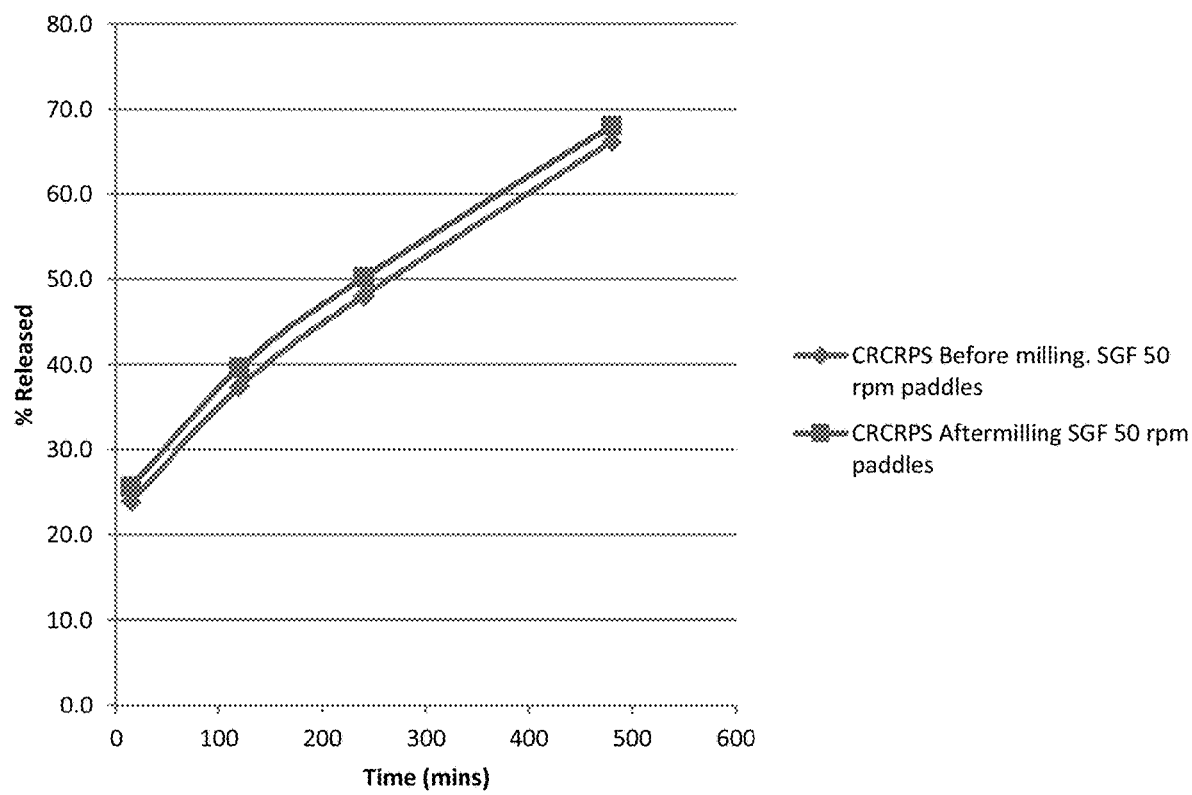

EXTENDED RELEASE, ABUSE DETERRENT DOSAGE FORMS

CROSS-REFERENCE TO RELATED APPLICATIONS

This application is a continuation of U.S. application Ser. No. 15/464,865, filed Mar. 21, 2017, which claims the priority of U.S. Provisional Application Ser. No. 62/315,952, filed Mar. 31, 2016, the disclosure of each is hereby incorporated by reference in its entirety.

FIELD

The present disclosure generally relates to extended release, abuse deterrent dosage forms comprising a plurality of crush-resistant controlled-release particles comprising an active ingredient, wherein the particles are prepared by a hot melt extrusion process.

BACKGROUND

Abuse of prescription drugs (particularly opioids) has become a serious societal problem. Such abuse places an enormous economic burden on society due to increased health care, work place, and criminal justice costs. Several routes of administration are commonly attempted by abusers. For example, the oral solid dosage form may be crushed or pulverized into a powder and administered by an intranasal route (i.e., snorted), or dissolved in a suitable solvent (e.g., water) and administered by a parenteral route (i.e., injected intravenously), swallowed after chewing in the mouth, or swallowed after physical manipulation.

Attempts have been made to diminish the abuse of opioid solid dosage forms. One approach has been to include in the dosage form an opioid antagonist that is not orally active but will substantially block the analgesic effects of the opioid if one attempts to dissolve the opioid and administer it parenterally. Another approach has been to include gel-forming high molecular weight polymers that confer plasticity to the dosage form rendering them difficult to crush and pulverize into powder. A commercially available extended release, abuse deterrent tablet of oxycodone HCl utilizes a physical barrier to deter both physical manipulations (e.g., reduction of the particle size using common household tools and chemical extraction of oxycodone HCl in an injectable solvent). However, these abuse deterrent tablets are still being abused by swallowing after chewing, swallowing after physical manipulation, and IV injection after the extraction of oxycodone HCl in a small volume of water (<10 mL) from both intact and cut tablets.

Thus, there is a need for oral dosage forms that provide extended release of the active ingredient yet are resistant to abuse by oral, intranasal, and IV injection via chewing, grinding, and chemical extraction.

SUMMARY

One aspect of the present disclosure encompasses an extended release, abuse deterrent dosage form comprising a plurality of particles and at least one pharmaceutically acceptable excipient. The plurality of particles comprises at least two plastic/elastic polymers and at least one active pharmaceutical ingredient (API) or a pharmaceutically acceptable salt thereof. The particles included in the dosage forms provide abuse deterrent features and provide extended release of the API.

Other aspects and iterations of the disclosure are described in more detail below.

BRIEF DESCRIPTION OF THE DRAWINGS

FIG. 1 presents the in vitro dissolution profiles of crush-resistant controlled-release particulate systems (CRCRPS) before and after grinding in a coffee grinder.

DETAILED DESCRIPTION

The present disclosure provides extended release dosage forms that have abuse deterrent properties. The dosage forms comprise crush-resistant controlled-release particles that are produced by hot melt extrusion. The crush-resistant controlled-release particles deter oral abuse by chewing, intranasal abuse by milling and grinding, and IV injection abuse after extraction of an active pharmaceutical ingredient. Also provided herein are processes for preparing the crush-resistant controlled-release particles and processes for preparing dosage forms comprising the crush-resistant controlled-release particles.

(I) Particles

One aspect of the present disclosure provides crush-resistant controlled-release particles. The particles comprise at least one plastic/elastic polymer and at least one pharmaceutical ingredient (API) or a pharmaceutically acceptable salt thereof. Typically, the particles further comprise at least one plasticizer, at least one lubricant, or combinations thereof. In some embodiments, the particles may further comprise at least one wetting agent. The particles are prepared by a hot melt extrusion process as detailed below in section (III)(a). The composition of the particles imparts sufficient mechanical integrity (e.g., hardness, resilience, etc.) such the particles are resistant to crushing, grinding, milling, or pulverizing to form a fine powder. Additionally, the particles have a slow rate of dissolution such that release of the API is extended, i.e., it proceeds over a span of hours. Thus, the particles disclosed herein are crush-resistant controlled-release particles (and are also known as a crush-resistant controlled-release particle system or CRCRPS).

The components of the crush-resistant controlled-release particles are detailed below.

(a) Plastic/Elastic Polymers

The crush-resistant controlled-release particles comprise at least one plastic/elastic polymer. A plastic/elastic polymer generally refers to a material that becomes pliable or moldable above a certain temperature and solidifies upon cooling.

The identity of the plastic/elastic polymer(s) included in the crush-resistant controlled-release particles can and will vary depending upon the desired properties (e.g., resilience to physical manipulation) of the particles. The plastic/elastic polymer may be synthetic, semi-synthetic, or natural; the plastic/elastic polymer may be soluble in water or insoluble in water. The weight average molecular weight distribution of the plastic/elastic polymer may range from about 20,000 to more than 7,000,000.

In some embodiments, the plastic/elastic polymer may be a polyvinyl ester such as, e.g., polyvinyl acetate, polyvinyl propionate, polyvinyl butyrate, and the like. An exemplary polyvinyl ester is polyvinyl acetate (PVAc), copolymers thereof, and derivatives thereof (e.g., polyvinyl alcohol). In embodiments in which the plastic/elastic polymer is polyvinyl acetate, the weight average molecular weight distribution of polyvinyl acetate can range from about 100,000 to about 500,000.

In other embodiments, the plastic/elastic polymer may be a poly-N-vinylamide, such as polyvinylpyrrolidone or polyvinyl caprolactam. An exemplary poly-N-vinylamide is polyvinylpyrrolidone (also called PVP or povidone) or copolymers thereof. The average molecular weight of polyvinylpyrrolidone can range from several thousand to about 1.5 million.

In further embodiments the plastic/elastic polymer may be a blend of polyvinyl acetate and polyvinylpyrrolidone (also called poly(vinylpyrrolidone-co-vinyl acetate) or polyvinyl acetate-polyvinylpyrrolidone). The weight ratio of polyvinyl acetate to polyvinylpyrrolidone may be about 1:9, about 2:8, about 3:7, about 4:6, about 5:5, about 6:4, about 7:3, about 8:2, or about 9:1. Blends of polyvinyl acetate-polyvinylpyrrolidone are available under the trade name KOLLIDON® VA64 (in which the ratio of polyvinylpyrrolidone to polyvinyl acetate is 6:4) or KOLLIDON® SR (in which the ratio of polyvinyl acetate to polyvinylpyrrolidone to about 4:1, i.e., contains about 80% of polyvinyl acetate having an average weight molecular weight distribution of about 450,000 and about 19% of polyvinylpyrrolidone having an average weight molecular weight distribution of about 50,000). The blend may further comprise sodium lauryl sulfate and/or silicon dioxide as stabilizer(s) or flowability agent(s).

In additional embodiments, the plastic/elastic polymer may be a polyalkylene oxide, such as polyethylene oxide, polypropylene oxide, copolymers, or derivatives thereof. An exemplary polyalkylene oxide is polyethylene oxide. The average weight molecular weight distribution of the polyethylene oxide can range from about 100,000 to 7 million or more.

In still other embodiments, the plastic/elastic polymer may be a cellulose derivative such as cellulose esters (e.g., cellulose acetate) or cellulose ethers. Non-limiting examples of suitable cellulose ethers include hydroxypropyl cellulose, hydroxypropylmethyl cellulose, methyl cellulose, ethyl cellulose, hydroxymethyl cellulose, hydroxyethyl cellulose, carboxymethyl cellulose, mixtures, and derivatives thereof. The average molecular weight distribution of cellulose ethers can range from about 20,000 to about 1.5 million.

In still other embodiments, the plastic/elastic polymer may be an acrylic acid polymer (i.e., polyacrylic acid), a methacrylic acid polymer, an acrylate polymer (e.g., methylacrylate polymer, ethylacrylate polymer), a methacrylate polymer (e.g., methyl methacylate polymer, etc.), a copolymer thereof, or a derivative thereof. Suitable polyacrylic acids include carbomers, which are homopolymers of acrylic acid cross linked with polyalcohol allyl ethers (e.g., allyl ether pentaerythritol, allyl ether of sucrose, or allyl ether of propylene), and polycarbophil, which is a homopolymer of acrylic acid cross linked with divinyl glycol. Examples of suitable copolymers include a copolymer of ethyl acrylate and methyl methacrylate, copolymer of ethyl acrylate, methyl methacrylate, and methacrylic acid ester with quaternary ammonium groups, copolymer of methacrylic acid and ethylacrylate, and the like.

Other suitable plastic/elastic polymers include polycarboxylic acids; polyamines, natural gums (e.g., polysaccharides derived from botanical sources or seaweeds, or produced via bacterial fermentation), starches, pectins, alginates, polypeptides (such as, e.g., gelatin, albumin, polylysine, soy protein, and so forth); and combinations thereof.

The amount of the plastic/elastic polymer(s) present in the crush-resistant controlled-release particles can and will vary depending upon the identity of the polymer and the desired properties (e.g., strength, mechanical integrity, rate of dissolution, and the like) of the particles. In general, the amount of plastic/elastic polymer present in the particles may range from about 30% to about 90% by weight of the particles. In various embodiments, the amount of plastic/elastic polymer may be about range from about 30% to about 40%, from about 40% to about 50%, from about 50% to about 60%, from about 60% to about 70%, from about 70% to about 80% by weight of the particles.

(b) Plasticizers

The crush-resistant controlled-release particles also comprise at least one plasticizer. In general, plasticizers increase the fluidity or flexibility of polymers, making them easier to handle or process. The plasticizer(s) included in the particles may be hydrophilic, hydrophobic, or a combination thereof. Examples of suitable plasticizers include but are not limited to glycerin (glycerol), polyethylene glycols (e.g., PEG 300, PEG 400, PEG 600, etc.), polyethylene glycol monomethyl ether, propylene glycol, sorbitol sorbitan solution, triethyl cellulose, dicarboxylic acid esters (e.g., sebacic acid, azelaic acid), acetyl tributyl citrate, acetyl triethyl citrate, castor oil, vegetable oils, diacetylated monoglycerides, dibutyl sebacate, diethyl phthalate, triacetin, tributyrin, tributyl citrate, triethyl citrate, polaxamers (i.e., triblock copolymers of polyethylene oxide and polypropylene oxide), or combinations thereof. In one embodiment, the plasticizer may be diethyl phthalate. In another embodiment, the plasticizer may be a combination of diethyl phthalate and polyethylene glycol.

The amount of plasticizer present in the particles can and will vary depending upon the identity of the plastic/elastic polymer(s) and the desired release properties of the particles. In general, the amount of plasticizer present in the particles may range from about 2% to about 75% by weight of the total weight of the plastic/elastic polymer. In various embodiments, the amount of plasticizer may range from about 2% to about 10%, from about 10% to about 30%, from about 30% to about 50%, or from about 50% to about 75% by weight of the total weight of the plastic/elastic polymer.

(c) Lubricants

The crush-resistant controlled-release particles also comprise at least one lubricant. Non-limiting examples of suitable lubricants include magnesium stearate, calcium stearate, zinc stearate, colloidal silicon dioxide, hydrogenated vegetable oils, sterotex, polyoxyethylene monostearate, polyethylene glycol, sodium stearyl fumarate, sodium benzoate, sodium lauryl sulfate, magnesium lauryl sulfate, light mineral oil, or combinations thereof. In one embodiment, the lubricant may be magnesium stearate.

The amount of lubricant present in the particles can and will vary depending upon the identity and amount of the other components. In general, the amount of lubricant may range from about 0.1% to about 3.0% by weight of the particles. In various embodiments, the amount of lubricant may range from about 0.2% to about 2.0%, from about 0.5% to about 1.5%, or from about 0.8% to about 1.2% by weight of the particles. In specific embodiments, the amount of the lubricant may be about 1% by weight of the particles.

(d) Wetting Agents

The crush-resistant controlled-release particles may further comprise at least one wetting agent. Wetting agents increase the spreading and penetrating properties of a liquid by lowering its surface tension. Suitable wetting agents include surfactants and/or emulsifiers. Non-limiting example of suitable surfactants include nonionic surfactants (e.g., polyoxyethylene glycol alkyl ethers, polyoxyethylene glycol sorbitan alkyl esters, polyethylene glycol esters, block co-polymers of polyethylene glycol and polypropylene glycol, polyoxyethylene fatty acid amides, ethoxylated aliphatic alcohols, alkylphenols, and the like), anionic surfactants (e.g., alkyl sulfates such as sodium lauryl sulfate or ammonium lauryl sulfate, alkyl sulfonates, alkyl benzene sulfonates, alpha sulfonyl fatty acids, alkyl phosphates, dioctyl sulfosuccinate, isethionates, alkyl ether sulfates, methyl sarcosines and the like), cationic surfactants (e.g., alkyltrimethylammonium bromide; cetyltrimethylammonium bromide, benzalkonium chloride; benzethonium chloride, and so forth), and zwitterionic surfactants (e.g., CHAPS, lecithin, cocoaminopropyl betaine, and so forth). Suitable emulsifiers include sorbitan fatty acid esters such as sorbitan monooleate or sorbitan monostearate, glyceryl fatty acid esters such as glyceryl monooleate or glyceryl monosteareate, polyethylene glycols, glycerol, block co-polymers of polyethylene glycol and polypropylene glycol, polaxamers, polysorbates, and the like). The amount of wetting agent present in the particles can and will vary depending upon the identity of the wetting agent and the other components of the particles.

The amount of wetting present in the particles can and will vary depending, for example, on the identity and amount of the other components present in the particles. In general, the amount of wetting agent present in the particles may range from about 2% to about 75% by weight of the total weight of the particles. In various embodiments, the amount of wetting agent may range from about 2% to about 10%, from about 10% to about 30%, from about 30% to about 50%, or from about 50% to about 75% by weight of the total weight of the particles.

(e) APIs

The crush-resistant controlled-release particles also comprise at least one API or a pharmaceutically acceptable salt thereof. Suitable APIs include, without limit, opioid analgesic agents (e.g., adulmine, alfentanil, allocryptopine, allylprodine, alphaprodine, anileridine, aporphine, benzylmorphine, berberine, bicuculine, bicucine, bezitramide, buprenorphine, bulbocaprine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphine, nalmefene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tapentadol, tilidine, and tramadol); opioid antagonists (e.g., naloxone, naltrexone, alvimopan, cyprodime, diprenorphine, gemazocine, 5'-guanidinonaltrindole, levallorphan, methylnaltrexone, naldemedine, nalmexone, nalorphine, naloxazone, naloxol, naloxonazine, 6β-naltrexol-d4, naltriben, naltrindole, norbinaltorphimine, oxilorphan, quadazocine, and samidorphan); non-opioid analgesic agents (e.g., acetylsalicylic acid, acetaminophen, paracetamol, ibuprofen, ketoprofen, indomethacin, diflunisol, naproxen, ketorolac, dichlophenac, tolmetin, sulindac, phenacetin, piroxicam, and mefamanic acid); anti-inflammatory agents (e.g., glucocorticoids such as alclometasone, fluocinonide, methylprednisolone, triamcinolone and dexamethasone; non-steroidal anti-inflammatory agents such as celecoxib, deracoxib, ketoprofen, lumiracoxib, meloxicam, parecoxib, rofecoxib, and valdecoxib); antitussive agents (e.g., dextromethorphan, codeine, hydrocodone, caramiphen, carbetapentane, and dextromethorphan); antipyretic agents (e.g., acetylsalicylic acid and acetaminophen); antibiotic agents (e.g., aminoglycosides such as, amikacin, gentamicin, kanamycin, neomycin, netilmicin, streptomycin, and tobramycin; carbecephem such as loracarbef; carbapenems such as certapenem, imipenem, and meropenem; cephalosporins such as cefadroxil cefazolin, cephalexin, cefaclor, cefamandole, cephalexin, cefoxitin, cefprozil, cefuroxime, cefixime, cefdinir, cefditoren, cefoperazone, cefotaxime, cefpodoxime, ceftazidime, ceftibuten, ceftizoxime, and ceftriaxone; macrolides such as azithromycin, clarithromycin, dirithromycin, erythromycin, and troleandomycin; monobactam; penicillins such as amoxicillin, ampicillin, carbenicillin, cloxacillin, dicloxacillin, nafcillin, oxacillin, penicillin G, penicillin V, piperacillin, and ticarcillin; polypeptides such as bacitracin, colistin, and polymyxin B; quinolones such as ciprofloxacin, enoxacin, gatifloxacin, levofloxacin, lomefloxacin, moxifloxacin, norfloxacin, ofloxacin, and trovafloxacin; sulfonamides such as mafenide, sulfacetamide, sulfamethizole, sulfasalazine, sulfisoxazole, and trimethoprim-sulfamethoxazole; tetracyclines such as demeclocycline, doxycycline, minocycline, and oxytetracycline); antimicrobial agents (e.g., ketoconazole, amoxicillin, cephalexin, miconazole, econazole, acyclovir, and nelfinavir); antiviral agents (e.g., acyclovir, gangciclovir, oseltamivir, and relenza); steroids (e.g., estradiol, testosterone, cortisol, aldosterone, prednisone, and cortisone); amphetamine stimulant agents (e.g., amphetamine and amphetamine-like drugs); non-amphetamine stimulant agents (e.g., methylphenidate, nicotine, and caffeine); laxative agents (e.g., bisacodyl, casanthranol, *senna*, and castor oil); anti-nausea agents (e.g., dolasetron, granisetron, ondansetron, tropisetron, meclizine, and cyclizine); anorexic agents (e.g., fenfluramine, dexfenfluramine, mazindol, phentermine, and aminorex); antihistaminic agents (e.g., phencarol, cetirizine, cinnarizine, ethamidindole, azatadine, brompheniramine, hydroxyzine, and chlorpheniramine); antiasthmatic agents (e.g., zileuton, montelukast, omalizumab, fluticasone, and zafirlukast); antidiuretic agents (e.g., desmopressin, vasopressin, and lypressin); antimigraine agents (e.g., naratriptan, frovatriptan, eletriptan, dihydroergotamine, zolmitriptan, almotriptan, and sumatriptan); antispasmodic agents (e.g., dicyclomine, hyoscyamine, and peppermint oil); antidiabetic agents (e.g., methformin, acarbose, miglitol, pioglitazone, rosiglitazone, nateglinide, repaglinide, mitiglinide, saxagliptin, sitagliptine, vildagliptin, acetohexamide, chlorpropamide, gliclazide, glimepiride, glipizide, glyburide, tolazamide, and tolbutamide); respiratory agents (e.g., albuterol, ephedrine, metaproterenol, and terbutaline); sympathomimetic agents (e.g., pseudoephedrine, phenylephrine, phenylpropanolamine, epinephrine, norepinephrine, dopamine, and ephedrine); H2 blocking agents (e.g., cimetidine, famotidine, nizatidine, and ranitidine); antihyperlipidemic agents (e.g., clofibrate, cholestyramine, colestipol, fluvastatin, atorvastatin, genfibrozil, lovastatin, niacin, pravastatin, fenofibrate, colesevelam, and simvastatin); antihypercholesterol agents (e.g., lovastatin, simvastatin, pravastatin, fluvastatin, atorvastatin, cholestyramine, colestipol, colesevelam, nicotinic acid, gemfibrozil, and ezetimibe); cardiotonic agents (e.g., digitalis, ubidecarenone, and dopamine); vasodilating agents (e.g., nitroglycerin, captopril, dihydralazine, diltiazem, and isosorbide dinitrate); vasoconstricting agents (e.g., dihydroergotoxine and dihydroergotamine); anticoagulants (e.g., warfarin, heparin, and Factor Xa inhibitors); sedative agents (e.g., amobarbital, pentobarbital, secobarbital, clomethiazole, diphenhydramine hydrochloride, and alprazolam); hypnotic agents (e.g., zaleplon, zolpidem, eszopiclone, zopiclone, chloral hydrate, and clomethiazole); anticonvulsant agents (e.g., lamitrogene, oxycarbamezine, phenytoin, mephenytoin, ethosuximide, methsuccimide, carbamazepine, valproic acid, gabapentin, topiramate, felbamate, and phenobarbital); muscle relaxing agents (e.g., baclofen, carisoprodol, chlorzoxazone, cyclobenzaprine, dantrolene sodium, metaxalone, orphenadrine, pancuronium bromide, and tizanidine); antipsychotic agents (e.g., phenothiazine, chlorpromazine, fluphenazine, perphenazine, prochlorperazine, thioridazine, trifluoperazine, haloperidol, droperidol, pimozide, clozapine, olanzapine, risperidone, quetiapine, ziprasidone, melperone, and paliperidone); antianxiolitic agents (e.g., lorazepam, alprazolam, clonazepam, diazepam, buspirone, meprobamate, and flunitrazepam); antihyperactive agents (e.g., methylphenidate, amphetamine, and dextroamphetamine); antihypertensive agents (e.g., alpha-methyldopa, chlortalidone, reserpine, syrosingopine, rescinnamine, prazosin, phentolamine, felodipine, propanolol, pindolol, labetalol, clonidine, captopril, enalapril, and lisonopril); anti-neoplasia agents (e.g., taxol, actinomycin, bleomycin A2, mitomycin C, daunorubicin, doxorubicin, epirubicin, idarubicin, and mitoxantrone); soporific agents (e.g., zolpidem tartrate, eszopiclone, ramelteon, and zaleplon); tranquilizer agents (e.g., alprazolam, clonazepam, diazepam, flunitrazepam, lorazepam, triazolam, chlorpromazine, fluphenazine, haloperidol, loxapine succinate, perphenazine, prochlorperazine, thiothixene, and trifluoperazine); decongestant agents (e.g., ephedrine, phenylephrine, naphazoline, and tetrahydrozoline); beta blockers (e.g., levobunolol, pindolol, timolol maleate, bisoprolol, carvedilol, and butoxamine); alpha blockers (e.g., doxazosin, prazosin, phenoxybenzamine, phentolamine, tamsulosin, alfuzosin, and terazosin); non-steroidal hormones (e.g., corticotropin, vasopressin, oxytocin, insulin, oxendolone, thyroid hormone, and adrenal hormone); erectile disfunction improvement agents; herbal agents (e.g., glycyrrhiza, aloe, garlic, nigella sativa, rauwolfia, St John's wort, and valerian); enzymes (e.g., lipase, protease, amylase, lactase, lysozyme, and urokinase); humoral agents (e.g., prostaglandins, natural and synthetic, for example, PGE1, PGE2alpha, PGF2alpha, and the PGE1 analog misoprostol); psychic energizers (e.g., 3-(2-aminopropy)indole and 3-(2-aminobutyl)indole); nutritional agents; essential fatty acids; non-essential fatty acids; vitamins; minerals; and combinations thereof.

Any of the above-mentioned APIs may be incorporated in the particles described herein in any suitable form, such as, for example, as a pharmaceutically acceptable salt, uncharged or charged molecule, molecular complex, solvate or hydrate, prodrug, and, if relevant, isomer, enantiomer, racemic mixture, and/or mixtures thereof. Furthermore, the API may be in any of its crystalline, semi-crystalline, amorphous, or polymorphous forms.

In one embodiment, the API present in the crush-resistant controlled-release particles may have a potential for abuse. For example, the API may be an opioid analgesic agent, a stimulant agent, a sedative agent, a hypnotic agent, an antianxiolitic agent, or a muscle relaxing agent.

In another embodiment, the API present in the crush-resistant controlled-release particles may be a combination of an opioid analgesic and a non-opioid analgesic. Suitable opioid and non-opioid analgesics are listed above.

In exemplary embodiments, the API in the crush-resistant controlled-release particles may be an opioid analgesic. Exemplary opioid analgesics include oxycodone, oxymorphone, hydrocodone, hydromorphone, codeine, morphine, or pharmaceutically acceptable salt thereof. In an exemplary embodiment, the API may be oxycodone hydrochloride. In another exemplary embodiment, the API may be oxymorphone hydrochloride.

The amount of API in the crush-resistant controlled-release particles can and will vary depending upon the active agent and the desired dose of API in the final dosage form. In general, the amount of API in the particles may range from about 2% to about 70% by weight of the particles. In various embodiments, the amount of API may range from about 2% to about 5%, from about 5% to about 10%, from about 10% to about 20%, from about 20% to about 30%, from about 30% to about 40%, from about 40% to about 50%, from about 50% to about 60%, or from about 60% to about 70% by weight of the particles.

(f) Exemplary Particles

In specific embodiments, the crush-resistant controlled-release particles may comprise a blend of polyvinyl acetate-polyvinylpyrrolidone, one or more plasticizers, a lubricant, optionally at least one wetting agent, and optionally a polyethylene oxide. The plasticizer may comprise diethyl phthalate and polyethylene glycol. The lubricant may be magnesium stearate. The optional wetting agent may be an alkyl sulfate or a sorbitan fatty acid ester. The polyethylene oxide may have an average molecule weight of about 100,000.

(g) Size of Particles

The size of the particles disclosed herein can and will vary. In general, the particles are too large to be inhaled or insufflated. Typically, the size distribution of the particles may range from about 50 micrometers (μm) to about 1500 μm. In some embodiments, the particle size distribution may range from about 100 lam to about 1000 μm. The particle distribution also can be described using D values. For example the D10 diameter is the diameter at which 10% of a sample's mass is comprised of smaller particles, and the D50 is the diameter at which 50% of a sample's mass is comprised of smaller particles. Thus, the D50 is the mass median diameter. In certain embodiments, the D50 of the particles may be about 150 μm, about 200 μm, about 300 μm, about 400 μm, about 450 μm, about 500 μm, about 550 μm, about 600 μm, about 650 μm, about 700 μm, about 750 μm, about 800 μm, about 850 μm, about 900 μm, about 950 μm, or about 1000 μm, and the D10 of the particles may be about 75 μm, about 100 μm, about 200 μm, about 300 μm, about 400 μm, about 500 μm, about 600 μm, about 700 μm, or about 800 μm.

(h) Physical Properties of the Particles

The particles disclosed herein are formed by a melt extrusion process (see section (III)(a) below). The combination of plastic/elastic polymers and other components in the particles imparts sufficient mechanical integrity (i.e., strength, hardness, etc.) such that the particles are resistant to crushing, grinding, milling, or pulverizing to form a fine powder or particles that are small enough to be snorted or insufflated. In general, particles suitable for insufflation are less than about 20 μm, less than about 10 μm, or less than about 5 μm. The particles formed by melt extrusion disclosed herein may be milled or ground in a coffee grinder, a coffee mill, a blender, a spice grinder, a pill crusher, as tablet grinder, a ball mill, a co-mill, a high-shear mill, or another apparatus to reduce particle size. After milling or grinding for a period of time ranging from about 15 seconds up to about 10 minutes, the D50 of the particles may be reduced by less than about than 5%, less than about 10%, less than about 15%, less than about 20%, less than about 25%, less than about 30%, less than about 35%, less than about 40%, or less than about 50%.

In some embodiments, the size of the particles formed by melt extrusion disclosed herein may increase as the grinding or milling time increases. For example, the average particle size of the plurality of particles increases after being ground or milled for more than about 3 minutes. While not being bound to a particular theory, it is hypothesized that the heat generated during the grinding or milling process is sufficient to melt the plastic/elastic polymers in the particles causing the particles or fragments thereof to agglomerate into larger sized particles.

In additional embodiments, the mechanical integrity of the particles may be accessed by measuring the breaking point or the breaking strength of the particles. The breaking point refers to the amount of applied force needed to compromise the integrity of the particle. The force necessary to determine the breaking point may be generated using a Texture Analyzer model TA.XT. Plus (Texture Technologies Corp.), an Instron Universal Tester (Instron Engineering Corp.), or other suitable instrument. The particles may exhibit a breaking point of greater than about 300 Newtons (N), greater that about 500 N, or greater than about 1000 N. Alternatively the particles may not exhibit a breaking point. Rather the particles may flatten or deform (without breaking) upon application of increasing force.

(i) In Vitro Release Profile of the Particles

The composition of the particles controls the rate of dissolution of the particles. In particular, the rate of dissolution of the particles disclosed herein is slow (i.e., is controlled by time). As a consequence, the rate of API release from the particles is slow or extended. Thus, the API is released from the particles over an extended period of time during in vitro dissolution testing. For example, the total amount of API may be released over a period of about 6 hours, over a period of about 12 hours, over a period of about 18 hours, or over a period of about 24 hours.

The in vitro dissolution of the API from the particles disclosed herein may be measured using an approved USP procedure. For example, dissolution may be measured using an USP approved Type 2 paddle apparatus, at a paddle speed of 50 rpm or 100 rpm, and a constant temperature of 37±0.5° C. The dissolution test may be performed in the presence of 500 mL, 900 mL, or 1,000 mL of a suitable dissolution medium (e.g., having a pH from about 1.0 to about 7.0). Non-limiting examples of suitable dissolution media include water, simulated gastric fluid (SGF), phosphate buffer (pH 6.8), acetate buffer (pH 4.5), and 0.1N HCl.

In various embodiments, the in vitro release of the API from the particles is such that no more than about 50%, 60%, 70%, 80%, 90% or 95% of the API is released within about 6 hours, 8 hours, 12 hours, 18 hours, or 24 hours. In one embodiment, no more than about 80% of the API is released within about 6 hours. In another embodiment, no more than about 80% of the API is released within about 8 hours. In a further embodiment, no more than about 80% of the API is released within about 12 hours. In yet another embodiment, no more than about 80% of the API is released within about 18 hours. In an alternate embodiment, no more than about 80% of the API is released within about 24 hours.

(II) Dosage Forms

Another aspect of the present disclosure encompasses dosage forms comprising the crush-resistant controlled-release particles described above in section (I). In general, the dosage form is a solid dosage form that is formulated for oral administration. The solid dosage form may be a tablet or a capsule. Suitable tablets include orally disintegrating/dissolving tablets, fast disintegrating/dissolving tablets, and conventional tablets.

(a) Tablets

In some embodiments, the dosage form is a tablet. The term "tablet" includes tablets, caplets, pills, compacts, and pellets of any shape or size that optionally may be scored. In certain iterations, the tablet may be an orally disintegrating/dissolving tablet (also called an orodispersible tablet or ODT), which disintegrates quickly in the mouth in the presence of saliva to be swallowed without the need for water. In other iterations, the tablet may be a fast disintegrating/dissolving tablet (FTD) or quickly disintegrating/dissolving tablet. The fast disintegrating/dissolving tablet can be swallowed intact and rapidly disintegrate in the stomach. Alternatively, the fast disintegrating/dissolving tablet can be readily dispersed in water to form a dispersion that is easy to swallow. In general, orally disintegrating/dissolving tablets and fast disintegrating/dissolving tablets disintegrate or disperse within less than about 3 minutes, less than about 2 minutes, less than about 1 minute, or less than about 30 seconds. However, even though the tablet may disintegrate quickly and release the particles, the properties of the particles do not change, i.e., they remain crush resistant and provide controlled release of the API. In still other iterations, the tablet may be a conventional tablet, i.e., a tablet that takes longer than about 3 minutes to disintegrate or dissolve.

The tablet dosage form comprises a plurality of the crush-resistant controlled-release particles disclosed herein and one or more pharmaceutically acceptable excipients. The pharmaceutically acceptable excipient(s) may be chosen from binders, fillers, super-disintegrants, lubricants, ion exchange resin powders, or combinations thereof. In some embodiments, the tablet may further comprise at least one aversive agent.

Binders.

In some embodiments, the tablet may comprise one or more binders. Non-limiting examples of suitable binders include starches (e.g., corn starch, potato starch, wheat starch, rice starch, and the like), pregelatinized starch, hydrolyzed starch, cellulose, microcrystalline cellulose, cellulose derivatives (e.g., methylcellulose, ethylcellulose, hydroxypropylcellulose, hydroxypropylmethylcellulose, sodium carboxymethylcellulose, and the like), saccharides (e.g., sucrose, lactose, and so forth), sugar alcohols (e.g., maltitol, sorbitol, xylitol, polyethylene glycol, and the like), alginates (e.g., alginic acid, alginate, sodium alginate, and so forth), gums (e.g., gum arabic, guar gum, gellan gum, xanthan gum, and the like), pectins, gelatin, C12-C18 fatty acid alcohols, polyvinylpyrrolidinone (also called copovidone), polyethylene oxide, polyethylene glycol, polyvinyl alcohols, waxes (e.g., candelilla wax, carnauba wax, beeswax, and so forth), or combinations of any of the forgoing. In embodiments in which binder is present in the tablet, the amount of binder may range from about 0.1% to about 50% by weight of the total weight of the tablet. In various embodiments, the amount of binder may range from about 0.1% to about 10%, from about 10% to about 20%, from about 20% to about 30%, from about 30% to about 40%, or from about 40% to about 50% by weight of the total weight of the tablet.

Fillers.

In other embodiments, the tablet may comprise one or more fillers (also called diluents). Suitable fillers include without limit cellulose, microcrystalline cellulose, cellulose ethers (e.g., ethyl cellulose, methyl cellulose, hydroxypropyl cellulose, hydroxypropyl methylcellulose, sodium carboxymethylcellulose, etc.), cellulose esters (i.e., cellulose acetate, cellulose butyrate, and mixtures thereof), starches (e.g., corn starch, rice starch, potato starch, tapioca starch, and the like), modified starches, pregelatinized starches, phosphated starches, starch-lactose, starch-calcium carbonate, sodium starch glycolate, glucose, fructose, sucrose, lactose, xylose, lactitol, mannitol, malitol, sorbitol, xylitol, maltodextrin, trehalose, calcium carbonate, calcium sulfate, calcium phosphate, calcium silicate, magnesium carbonate, magnesium oxide, talc, or combinations thereof. In certain embodiments, the filler may also function as a taste-masking agent. Taste-masking agents include cellulose ethers, polyethylene glycols, polyvinyl alcohol, polyvinyl alcohol and polyethylene glycol copolymers, monoglycerides or triglycerides, acrylic polymers, mixtures of acrylic polymers with cellulose ethers, cellulose acetate phthalate, and combinations thereof. In embodiments in which filler is present in the tablet, the amount of filler may range from about 0.1% to about 50% by weight of the total weight of the tablet. In certain embodiments, the amount of filler may range from about 0.1% to about 10%, from about 10% to about 20%, from about 20% to about 30%, from about 30% to about 40%, or from about 40% to about 50% by weight of the total weight of the tablet.

Super-Disintegrants.

In further embodiments, the tablet may comprise one or more super-disintegrants. Non-limiting examples of suitable super-disintegrants include povidone, crospovidone, croscarmellose sodium, sodium starch glycolate, modified starches, modified cellulose, low substituted hydroxypropyl cellulose, calcium silicate, or combinations thereof. The amount of super-disintegrant included in the tablet may range from about 0.5% to about 50% by weight of the total weight of the tablet. In embodiments in which a binder is present in the tablet, the amount of binder may range from about 0.5% to about 10%, from about 10% to about 20%, from about 20% to about 30%, from about 30% to about 40%, or from about 40% to about 50% by weight of the total weight of the tablet.

Lubricants.

In still other embodiments, the tablet may comprise one or more lubricants. Non-limiting examples of suitable lubricants include magnesium stearate, calcium stearate, zinc stearate, colloidal silicon dioxide, hydrogenated vegetable oils, sterotex, polyoxyethylene monostearate, polyethylene glycol, sodium stearyl fumarate, sodium oleate, sodium benzoate, sodium lauryl sulfate, magnesium lauryl sulfate, light mineral oil, or combinations thereof. The amount of lubricant present in the tablet may range from about 0.1% % to about 3.0% by total weight of the tablet. In various embodiments, the amount of lubricant may range from about 0.1% to about 0.5%, from about 0.5% to about 1.0%, from about 1.0% to about 1.5.5% to about 3.0% by total weight of the tablet.

Ion-Exchange Resins.

In alternate embodiments, the tablet may comprise one or more ion exchange resin powders. The ion exchange resin powder is selected such that it can bind the API if the tablet (or fragments thereof) is contacted with a suitable solvent, thereby deterring abuse. Most ion exchange resins are based on crosslinked polystyrene or crosslinked acrylic or methacrylic acid polymers that are modified to contain functional groups. The ion exchange resin can be anionic or cationic. Cation resins may be weakly acidic (e.g., featuring carboxylic groups) or strongly acidic (e.g., featuring sulfonic acid groups). Anion resins may be weakly basic (e.g., featuring primary, secondary, and/or ternary amino groups) or strongly basic (e.g., featuring quaternary amino groups). In embodiments in which the tablet contains an ion exchange resin powder, the amount of ion exchange resin powder may range from about 0.5% to about 25% by weight of the total weight of the tablet. In various embodiments, the amount of ion exchange resin powder may range from about 0.5% to about 2%, from about 2% to about 5%, from about 5% to about 10%, from about 10% to about 15%, from about 15% to about 20%, or from about 20% to about 25% by weight of the total weight of the tablet.

Aversive Agents.

In certain embodiments, the tablet may further comprise one or more aversive agents to deter abuse of the dosage form. The aversive agent may be an irritant, a bittering agent, an emetic, a dye, or a combination thereof. In some embodiments, the aversive agent may be an irritant that causes irritation of mucous membranes located anywhere on or in the body, including membrane of the nose, mouth, eyes, and intestinal tract. Non-limiting examples of suitable irritants, include surfactants (e.g., sodium lauryl sulfate, alkylbenzene sulfonate, sodium laureth sulfate, triethanol ammonium lauryl sulfate, benzalkyonium chloride), poloxamers, sorbitan monostearate, sorbitan monooleate, glyceryl monostearate, glyceryl monooleate, mustard, allyl isothiocyanate, p-hydroxybenzyl isothiocyanate, piperine, niacin, capsaicin, capsaicin analogs (e.g., resiniferatoxin, tinyatoxin, heptanoylisobutylamide, heptanoyl guaiacylamide, dihydrocapsaicin, nordihydrocapsaiscin, homocapsaicin, homodihydrocapsaicin; homovanillyl octylester, nonanoyl vanillylamide), or combinations of any of the foregoing. In other embodiments, the aversive agent may be a bittering agent that imparts a bitter smell or bitter taste to the tablets or dispersions derived from the tablets. Examples of suitable bittering agents include without limit denatonium benzoate, denatonium saccharide, denatonium chloride, quinine sulfate, sucrose derivative (e.g., sucrose octaacetate), chlorosucrose derivatives, benzoic benzylamine amide, trichloroanisole, methyl anthranilate, alkaloids (e.g., sparteine, lupinine), quassinoids (e.g., asquassin, brucine), flavonoids (e.g., quercetin, naringen), or mixtures thereof. In further embodiments, the aversive agent may be an emetic. In general, the emetic is encapsulated or physically separated from the other components of the tablet such that it has no effect unless the tablet is subjected to physical tampering or manipulation. Non-limiting examples of suitable emetics include zinc sulfate, apomorphine, xylazine, emetine, ipecac derivatives, or combinations thereof. In yet additional embodiments, the aversive agent may be a dye or coloring agent. Suitable dyes include, without limitation, FD&C Blue No. 2, iron oxides, FD&C Red No. 3, FD&C Red No. 20, FD&C Yellow No. 6, FD&C Blue No. 1, FD&C Green No. 1, FD&C Green No. 3, FD&C Green No. 5, FD&C Red No. 30, D&C Orange No. 5, D&C Red No. 8, D&C Red No. 33, natural coloring agents such as grape skin extract, beet red powder, beta-carotene, annato, carmine, turmeric, paprika, or combinations thereof. In embodiments in which the tablet comprises an aversive agent, the amount of aversive agent may range from about 0.5% to about 15% by weight of the total weight of the tablet. In certain embodiments, the amount of aversive agent may range from about 0.5% to about 3%, from about 3% to about 6%, from about 6% to about 10%, or from about 10% to about 15% by weight of the total weight of the tablet.

The amount of crush-resistant controlled-release particles present in the tablet can and will vary depending upon the identity of the API and the desired dose of API in the tablet. In general, the amount of particles present in the tablet may range from about 30% to about 95% by weight of the total weight of the tablet. In various embodiments, the amount of particles present in the tablet may range from about 30% to about 40%, from about 40% to about 50%, from about 50% to about 60%, from about 60% to about 70%, from about 70% to about 80%, from about 80% to about 90%, or from about 90% to about 95% by weight of the total weight of the tablet. In various embodiments, the total amount of API in the tablet may range from about 1 mg to about 400 mg. In embodiments in which the API is an opioid analgesic, the amount of opioid in the tablet may range from about 2 mg to about 160 mg. In various embodiments, the amount of opioid in the tablet may range from about 2 mg to about 10 mg, from about 10 mg to about 40 mg, from about 40 mg to about 80 mg, or from about 80 mg to about 160 mg. In certain embodiments, the amount of opioid in the tablet may be about 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 45 mg, 50 mg, 60 mg, 70 mg, 80 mg, 100 mg, 120 mg, 140 mg, or 160 mg.

In one embodiment, the tablet comprises crush-resistant controlled-release particles, binder, filler, super-disintegrant, and/or lubricant. In another embodiment, the tablet comprises crush-resistant controlled-release particles, binder, filler, super-disintegrant, lubricant, and ion exchange resin powder. In an additional embodiment, the tablet comprises crush-resistant controlled-release particles, binder, filler, super-disintegrant, lubricant, and a nasal irritant as an aversive agent. The nasal irritant may sodium lauryl sulfate. In yet another embodiment, the tablet comprises crush-resistant controlled-release particles, binder, filler, super-disintegrant, lubricant, ion exchange resin powder, and a nasal irritant.

(b) Capsules

In other embodiments, the dosage form is a capsule. Typically, the capsule is a hard capsule. The shell of the capsule may comprise gelatin, hydrolyzed starch, or a cellulose derivative such as hydroxypropylmethylcellulose (also called hypromellose).

In some embodiments, the capsule consists of a plurality of the crush-resistant controlled-release particles. In other embodiments, the capsule comprises a plurality of particles and one or more pharmaceutically acceptable excipients. The pharmaceutically acceptable excipient(s) may be chosen from gelling polymers, fillers, effervescent systems, glidants, ion exchange resin powders, or combinations thereof. In some embodiments, the capsule comprising one or more excipients may further comprise at least one aversive agent.

Gelling Polymers.

In some embodiments, the capsule may comprise one or more gelling polymers. In general, the gelling polymer is a hydrophilic gelling polymer, which has affinity for water such that, when in contact with water or a suitable solvent, it readily absorbs water or solvent and/or swells to form a viscous mixture or gel. The resultant viscous mixture, therefore, is difficult to draw into a syringe, making it difficult or impossible to inject the mixture and/or extract the API from the mixture. The gelling polymer, therefore, is included in the capsule dosage form to deter abuse of the formulation. Non-limiting examples of suitable hydrophilic gelling polymers include cellulose ethers (e.g., hydroxypropylcellulose, hydroxypropylmethylcellulose, sodium carboxymethyl cellulose, methylcellulose, hydroxyethylcellulose, and the like), polyalkylene oxides (e.g., polyethylene oxide, polypropylene oxide, derivatives thereof, copolymers thereof, or combinations thereof), natural gums (e.g., glucomannan, guar gum, gum arabic, gum tragacanth, tara gum, alginate, alginic acid, fucoidan, laminarin, agar, carrageenans, xanthan gum, gellan gum, dextran, welan gum, diutan gum, pullulan, derivatives thereof, or combinations thereof), polyacrylic acids or crosslinked polyacrylic acids (e.g., carbomers), polyvinyl alcohol, polyvinylpyrrolidone, polyamines, or combinations of any of the foregoing. The average molecular weight of the gelling polymer may range from about 30,000 to about 15,000,000. In embodiments in which a gelling polymer is present in the capsule, the amount of gelling polymer may range from about 0.1% to about 50% by weight of the contents of the capsule. In some embodiments, amount of gelling polymer may range from about 0.1% to 10%, from about 10% to about 20%, from about 20% to about 30%, from about 30% to about 40%, or from about 40% to about 50% by weight of the contents of the capsule.

Fillers.

In other embodiments, the capsule may comprise one or more fillers (also called diluents). Suitable fillers include without limit cellulose, microcrystalline cellulose, cellulose derivatives (e.g., calcium carboxymethyl cellulose, ethyl cellulose), starch, modified starches, pregelatinized starch, glucose/dextrose, fructose, sucrose, lactose, mannitol, sorbitol, xylitol, calcium carbonate, calcium sulfate, calcium phosphate, calcium silicate, magnesium carbonate, magnesium oxide, or combinations thereof. In embodiments in which filler is present in the capsule, the amount of filler may range from about 0.1% to about to about 50% by weight of the contents of the capsule. In various embodiments, the amount of filler may range from about 0.1% to about 10%, from about 10% to about 20%, from about 20% to about 30%, from about 30% to about 40%, or from about 40% to about 50% by weight of the contents of the capsule.

Effervescent Systems.

In still other embodiments, the capsule may comprise an effervescent system. As used herein, an "effervescent system" refers to a system generally comprising an acid component and a base component, wherein the system liberates carbon dioxide upon contact with an aqueous solution. The acid component of the effervescent system may be an organic acid, an inorganic acid, or combinations thereof. Non-limiting examples of suitable acids include adipic acid, ascorbic acid, benzoic acid, citric acid, disodium pyrophosphate, fumaric acid, glutaric acid, hexamic acid, lactic acid, lauric acid, malic acid, maleic acid, malonic acid, oxalic acid, phthalic acid, potassium bitartrate, sodium acid pyrophosphate, sodium dihydrogen phosphate, sorbic acid, succinic acid, tartaric acid, or combinations thereof. The base component of the effervescent system may be a base chosen from a carbonate, a bicarbonate, or combinations thereof. Examples of suitable bases include, without limit, ammonium bicarbonate, potassium bicarbonate, sodium bicarbonate, arginine carbonate, ammonium carbonate, calcium carbonate, lysine carbonate, potassium magnesium carbonate, sodium carbonate, sodium glycine carbonate, sodium sesquicarbonate, zinc carbonate, or combinations thereof. The mole ratio of the acid component to the base component in the effervescent system may be about 1:3, about 1:2, about 1:1, about 2:1, about 3:1, or any ratio in-between. In embodiments in which an effervescent system is present in the capsule, the amount of effervescent system may range from about 1% to about to about 50% by weight of the contents of the capsule. In various embodiments, the amount of effervescent system may range from about 1% to about 10%, from about 10% to about 20%, from about 20% to about 30%, from about 30% to about 40%, or from about 40% to about 50% by weight of the contents of the capsule.

Glidants.

In alternate embodiments, the capsule may comprise one or more glidants. Glidants improve the flowability of powders or granular mixtures. Non-limiting examples of suitable glidants include colloidal silica, colloidal silicon dioxide, cellulose, calcium phosphate (di or tri basic), fumed silica, hydrated magnesium carbonate, sodium silioaluminate, starch, talc, micronized talc, or combinations thereof. In embodiments in which a glidant is present in the capsule, the amount of glidant may range from about 0.1% to about to about 10% by weight of the contents of the capsule. In certain embodiments, the amount of may range from about 0.1% to about 0.5%, from about 0.5% to about 1.0%, from about 1.0% to about 1.5.5% to about 3.0% by total weight of the contents of the capsule.

Ion-Exchange Resins.

In yet other embodiments, the capsule may comprise one or more ion exchange resin powders. The ion exchange resin powder is selected such that it can bind the API if the capsule (or contents thereof) is contacted with a suitable solvent, thereby deterring abuse. The ion exchange resin powder can be anionic or cationic. Anion resins may be weakly acidic (e.g., featuring carboxylic groups) or strongly acidic (e.g., featuring sulfonic acid groups). Cation resins may be weakly basic (e.g., featuring primary, secondary, and/or ternary amino groups) or strongly basic (e.g., featuring quaternary amino groups). In embodiments in which the capsule contains an ion exchange resin powder, the amount of ion exchange resin powder may range from about 0.5% to about 25% by weight of the contents of the capsule. In various embodiments, the amount of ion exchange resin powder may range from about 0.5% to about 2%, from about 2% to about 5%, from about 5% to about 10%, from about 10% to about 15%, from about 15% to about 20%, or from about 20% to about 25% by weight of the contents of the capsule.

Aversive Agents.

In certain embodiments, the capsule may further comprise an aversive agent to deter abuse of the dosage form. The aversive agent may be an irritant, a bittering agent, an emetic, a dye, or a combination thereof. In some embodiments, the aversive agent may be an irritant that causes irritation of mucous membranes located anywhere on or in the body, including membrane of the nose, mouth, eyes, and intestinal tract. Non-limiting examples of suitable irritants, include surfactants (e.g., sodium lauryl sulfate, alkylbenzene sulfonate, sodium laureth sulfate, triethanol ammonium lauryl sulfate, benzalkyonium chloride), poloxamers, sorbitan monostearate, sorbitan monooleate, glyceryl monostearate, glyceryl monooleate, mustard, allyl isothiocyanate, p-hydroxybenzyl isothiocyanate, piperine, niacin, capsaicin, capsaicin analogs (e.g., resiniferatoxin, tinyatoxin, heptanoylisobutylamide, heptanoyl guaiacylamide, dihydrocapsaicin, nordihydrocapsaiscin, homocapsaicin, homodihydrocapsaicin; homovanillyl octylester, nonanoyl vanillylamide), or combinations of any of the foregoing. In other embodiments, the aversive agent may be a bittering agent that imparts a bitter smell or bitter taste to the tablets or dispersions derived from the tablets. Examples of suitable bittering agents include without limit denatonium benzoate, denatonium saccharide, denatonium chloride, quinine sulfate, sucrose derivative (e.g., sucrose octaacetate), chlorosucrose derivatives, benzoic benzylamine amide, trichloroanisole, methyl anthranilate, alkaloids (e.g., sparteine, lupinine), quassinoids (e.g., asquassin, brucine), flavonoids (e.g., quercetin, naringen), or mixtures thereof. In further embodiments, the aversive agent may be an emetic. In general, the emetic is encapsulated or physically separated from the other components of the capsule such that it has no effect unless the capsule is tampering with or manipulated. Non-limiting examples of emetics include zinc sulfate, apomorphine, xylazine, emetine, ipecac derivatives, or combinations thereof. In yet additional embodiments, the aversive agent may be a dye or coloring agents. Suitable dyes include, without limitation, FD&C Blue No. 2, iron oxides, FD&C Red No. 3, FD&C Red No. 20, FD&C Yellow No. 6, FD&C Blue No. 1, FD&C Green No. 1, FD&C Green No. 3, FD&C Green No. 5, FD&C Red No. 30, D&C Orange No. 5, D&C Red No. 8, D&C Red No. 33, natural coloring agents such as grape skin extract, beet red powder, beta-carotene, annato, carmine, turmeric, paprika, or combinations thereof. In embodiments in which the capsule comprises an aversive agent, the amount of aversive agent may range from about 0.5% to about 15% by weight of the total weight of the contents of the capsule. In certain embodiments, the amount of aversive agent may range from about 0.5% to about 3%, from about 3% to about 6%, from about 6% to about 10%, or from about 10% to about 15% by weight of the total weight of the contents of the capsule.

The amount of crush-resistant controlled-release particles present in the capsule can and will vary depending upon the identity of the API and the desired dose of API in the capsule. In general, the amount of crush-resistant controlled-release particles present in the capsule may range from about 5% to about 100% by weight of the contents of the capsule. In various embodiments, the amount of particles present in the capsule may range from about 5% to about 15%, from about 15% to about 3-%, from about 30% to about 40%, from about 40% to about 50%, from about 50% to about 60%, from about 60% to about 70%, from about 70% to about 80%, from about 80% to about 90%, or from about 90% to about 100% by weight of the contents of the capsule. In various embodiments, the total amount of API in the capsule may range from about 1 mg to about 400 mg. In embodiments in which the API is an opioid analgesic, the amount of opioid in the capsule may range from about 2 mg to about 160 mg. In various embodiments, the amount of opioid in the capsule may range from about 2 mg to about 10 mg, from about 10 mg to about 40 mg, from about 40 mg to about 80 mg, or from about 80 mg to about 160 mg. In certain embodiments, the amount of opioid in the tablet may be about 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 45 mg, 50 mg, 60 mg, 70 mg, 80 mg, 100 mg, 120 mg, 140 mg, or 160 mg.

In one embodiment, the capsule consists of crush-resistant controlled-release particles. In another embodiment, the capsule comprises crush-resistant controlled-release particles, gelling polymer, filler, effervescent system, and/or glidant. In still another embodiment, the capsule comprises crush-resistant controlled-release particles, gelling polymer, filler, effervescent system, glidant, ion exchange resin powder, and/or nasal irritant as an aversive agent. The nasal irritant may be sodium lauryl sulfate.

(c) In Vitro Release Profile of the Dosage Forms

The rate of dissolution of the dosage forms described above can and will vary depending on the type and/or amount of pharmaceutically acceptable excipients that may be present. In some embodiments, the dosage form may disintegrate or dissolve very rapidly. The rate of release of the API from the dosage form, however, parallels the rate of API release from the crush-resistant controlled-release particles. As detailed in section (I)(i) above, in vitro release of the API from the particles occurs over an extended period of time. Thus, in vitro release of the API from the dosage form also occurs over an extended period of time. For example, the total amount of API in the dosage form may be released over about 8 hours, over about 12 hours, over about 18 hours, or over about 24 hours.

(d) Abuse Deterrent Properties of the Dosage Forms

In embodiments in which the dosage form is tablet, the tablet may be crushed, ground, milled, or pulverized, but the crush-resistant particles will not be affected by the crushing, grinding, milling, or pulverizing (see section (I)(h) above). Likewise, in embodiments in which the dosage form is a capsule and the contents are removed from the capsule, the crush-resistant particles remain resistant to crushing, grinding, milling, or pulverizing. The crush-resistant particles, therefore, deter intranasal abuse by grinding or milling and/or deter oral abuse by chewing (pulverizing).

The dosage forms may also contain other agents that help deter abuse. In some embodiments, the dosage form may contain a gelling polymer or a binder/filler that forms a viscous mixture or gel when said dosage form is contacted with a small volume (<10 ml) of suitable solvent. The resultant viscous mixture is difficult to draw into a syringe, thereby deterring abuse by intravenous injection. Additionally, the API is difficult to extract from said viscous mixture, deterring intravenous injection or oral abuse after extraction of the API.

In other embodiments, the dosage form may contain an ion exchange resin powder that binds the API when said dosage form is contacted with a suitable solvent. The resultant homogenous solution is devoid of API, thereby deterring abuse by intravenous injection.

In still other embodiments, the dosage form may contain an aversive agent (e.g., irritant, bittering agent, emetic, and/or dye). The aversive agent makes oral, parental, or nasal administration of a tampered dosage form aversive or unpleasant.

(III) Processes for Preparing Particles and Dosage Forms

Also provided herein are processes for preparing the crush-resistant controlled release particles and dosage forms comprising the crush-resistant controlled release particles.

(a) Preparing Particles

The crush-resistant controlled-release particles described above in section (I) are prepared by a hot melt extrusion process. Hot melt extrusion (HME) is the process of applying heat and pressure to melt a polymer and force it though an orifice in a continuous process. Examples of pharmaceutical-class extruders, principles of operation, and process technology are detailed in Crowley et al. (Drug Development and Industrial Pharmacy, 2007, 33(9):909-926). The particles disclosed herein are prepared by a process comprising blending the plastic/elastic polymer(s), the API or salt thereof, and other components of the particles to form a blend, hot melt extruding the blend to form an extrudate, and pelletizing/milling the extrudate to form the particles.

The first step of the process comprises blending the components of the particles. Examples of suitable plastic/elastic polymers, plasticizers, lubricants, wetting agents, and APIs are provided above in sections (I)(a)-(e). The components may be combined in any order or may be premixed in various combinations before being combined together and blended. For example, the plastic/elastic polymers may be blended with liquid plasticizers and/or wetting agents prior to being blended with the other components. The components can be blended by mixing, roller mixing, drum mixing, shear mixing, dry blending, chopping, milling, granulating, dry granulating (e.g., slugging or roller compacting), wet granulating (e.g., fluid bed granulating, high shear granulating), and other mixing techniques known in the art, thereby forming a blend.

The next step of the process comprises hot melt extruding the blend to form an extrudate. In general, the hot melt extruding is performed using conventional screw extruders, e.g., single screw extruder or twin-screw-extruder. Temperatures may range from about 60° C. to about 250° C. with a pressure range of 0 to 150 bar. In some embodiments, the extrudate may be cooled and/or dried by conventional means.

The final step of the process comprises pelletizing/milling the extrudate to form particles. The extrudate can be cut into pieces by means of revolving or rotating knives, water jet cutters, wires, blades or with the assistance of laser cutter. Rod-shaped extrudate can be chopped into pellets or granules using a pelletizing machine. Alternatively, the extrudate can be press-molded into the desired pellet shape. Extrudate pieces or pellets can be milled in a milling machine (e.g., vertical mill, horizontal mill) to form particles having an average particle size distribution from about 50 micrometers to about 1500 micrometers.

(b) Preparing Tablets

The tablets comprising the hot melt extruded particles can be prepared using conventional methods known to those in the field of pharmaceutical formulation and described in the pertinent texts, e.g., in Gennaro, A. R., editor. "Remington: The Science & Practice of Pharmacy", 21st ed., Williams & Williams, and in the "Physician's Desk Reference", 2006, Thomson Healthcare. In particular, tablets comprising the hot melt extruded particles described above are prepared by blending the components of the tablet to form a mixture, forming the mixture into tablets, and optionally coating the tablets with a film coating.

The first step comprises blending the hot melt extruded particles described above with additional tablet components (i.e., binder, filler, super-disintegrant, lubricant, ion exchange resin powder, and/or aversive agent) described above in section (II)(a). The components can be combined in any order or may be premixed in various combinations before being combined together. The components can be blended by mixing, roller mixing, drum mixing, shear mixing, dry blending, chopping, milling, granulating, dry granulating (e.g., slugging or roller compacting), wet granulating (e.g., fluid bed granulating, high shear granulating), and other mixing techniques known in the art.

The process further comprises forming the mixture into a tablet. Tablet forming techniques are well known in the art. The tablet may be a compression tablet, a molded tablet, a compacted tablet, or a pressed tablet. The shape and size of the tablet may vary. In a preferred embodiment, the tablet may be formed by direct compression. The amount of compression applied to the mixture can and will vary depending upon the desired dissolution profile of the tablet.

The tablet may be coated with a film coating. The film coating does not affect the extended release or abuse deterrent properties of the tablet dosage forms. The film coating may be spray coated onto the dosage form. The spray coating system by be a bottom spray coating system, a top spray coating system, a tangential spray coating system, a pan coating system, or another suitable coating system.

Film coatings are well known in the art, e.g., some are commercially available, e.g., under the trade name OPADRY®. Typically, a film coating comprises at least one water-soluble polymer and at least one plasticizer. Non-limiting examples of suitable polymers include hydroxypropylmethyl cellulose, hydroxypropyl cellulose, hydroxypropylethyl cellulose, ethyl cellulose, methyl cellulose, cellulose acetate phthalate, microcrystalline cellulose and carrageenan, acrylic polymers, polyvinyl alcohol, anionic and cationic polymers of methacrylic acid, copolymers of methacrylates, copolymers of acrylates and methacrylates, copolymers of ethacrylate and methyl methacrylate, polyvinylacetate phthalate, and shellac. Examples of suitable plasticizers include, without limit, triethyl citrate (TEC), acetyltriethyl citrate (ATEC), acetyl tri-n-butyl citrate (ATBC), dibutyl sebacate, diethyl phthalate, and triacetin. The film coating may optionally comprise additional agents such as coloring agents, fillers, flavoring agents, taste-masking agents, surfactants, anti-tacking agents, and/or anti-foaming agents. Suitable examples of these agents are well known in the art.

(c) Preparing Capsules

The capsules containing the hot melt extruded particles are prepared assembling and encapsulating the components into the capsules. Means for preparing and filling hard-shelled capsules are well known in the art.

In some embodiments, the process comprises encapsulating the hot melt extruded particles into capsules. In other embodiments, the process comprises blending the hot melt extruded particles with other capsule components (i.e., gelling polymer, filler, effervescent system, glidant, ion exchange resin powder, and/or aversive agent) to form a mixture and then encapsulating the mixture into capsules.

Definitions

Compounds useful in the compositions and methods include those described herein in any of their pharmaceutically acceptable forms, including isomers such as diastereomers and enantiomers, salts, solvates, and polymorphs, as well as racemic mixtures and pure isomers of the compounds described herein, where applicable.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The term "about," particularly in reference to a given quantity, is meant to encompass deviations of plus or minus five percent.

As used herein, "abuse deterrent" refers to any property or feature of a pharmaceutical composition that lessens the potential for abuse of the active ingredient(s) in the composition.

EXAMPLES

The following examples are included to demonstrate preferred embodiments of the present disclosure. It should be appreciated by those of skill in the art that the techniques disclosed in the examples represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

Example 1: Crush-Resistant Controlled-Release Particle System (CRCRPS)

A crush-resistant controlled-release particulate system (CRCRPS) was prepared by a hot melt extrusion and milling process. The composition of the CRCRPS is provided in Table 1. KOLLIDON® SR contains 80% polyvinyl acetate (MW 450,000), 19% povidone (MW 50,000), 0.8% sodium lauryl sulfate, and 0.2% silicon dioxide. The ingredients were dry blended and hot melt extruded on a Pharma 11 twin screw extruder with temperatures as high as 130° C. with a pressure of 25 bar. The extrudate was milled into particles of the desired particle size distribution. The D50 of the particles was about 800 µm.

TABLE 1

Compositions of CRCRPS

| Material | % | mg/dosage |
| --- | --- | --- |
| Oxycodone HCL | 14 | 40 |
| KOLLIDON ® SR | 60-65 | 171.4-185.7 |
| Diethyl phthalate | 9-14.25 | 25.7-40.7 |
| Polyethylene Glycol 300 | 0.75-6 | 2.1-17.1 |
| Polyethylene Oxide N10 (MW 100,000) | 0-5 | 0-14.3 |
| Magnesium stearate | 1 | 2.86 |

Example 2: In Vitro Dissolution Profile of CRCRPS Before and after Grinding

An aliquot of CRCRPS (prepared as described in Example 1) was ground for 2 minutes in a coffee grinder. Particle size before and after grinding was determined using a Malvern particle size analyzer. The D10 and D50 values before and after grinding are presented in Table 2. The particle size was reduced only 20-25% after two minutes of grinding.

TABLE 2

Crush Resistance of CRCRPS

| | D10 µm | D50 µm |
| --- | --- | --- |
| Before grinding | 590 | 818 |
| After grinding | 442 | 654 |

The in vitro dissolution profile of CRCRPS before and after grinding was measured in 900 mL of simulated gastric fluid (SGF) using an USP type 2 paddle apparatus with a paddle speed of 50 rpm and a constant temperature of 37° C. Samples were removed at various time points from 0.2 hr to 8 hr and analyzed by HPLC for oxycodone hydrochloride. FIG. 1 presents the dissolution profiles of CRCRPS before and after grinding in a coffee grinder. The dissolution profile of the "ground" CRCRPS mirrored that of the "intact" particles. Both samples exhibited extended release, i.e., released less than 70% of oxycodone HCL within 8 hr.

Example 3: Effects of Grinding on Particle Size Distribution

Aliquots of CRCRPS (as prepared in Example 1) were ground for 60 seconds, 180 seconds, or 255 seconds and the percentage of particles of various sizes was estimated by screening. A shown in Table 3, the percentage of large particles (i.e., retained by 25 mesh screen or being >0.71 mm) increased after more than 3 minutes of grinding.

TABLE 3

Effect of Grinding Time on Particle Size Distribution

| | Milling Time (s) | Weight (g) | >0.71 mm % | >0.25 mm % | >20 µm % |
|---|---|---|---|---|---|
| 1 | 60 | 3.000 | 57.8 | 39.9 | 2.3 |
| 2 | 180 | 2.9213 | 44.8 | 52.3 | 2.7 |
| 3 | 255 | 2.917 | 77.1 | 22.2 | 0.8 |

Increasing amounts of CRCRPS (i.e., 1x dosage to 20x dosage) were ground for 3 minutes. The results are shown in Table 4.

TABLE 4

Effect of Mass on Particle Size Distribution

| | Milling Time (s) | Weight (g) | >0.71 mm % | >0.25 mm % | >20 µm % |
|---|---|---|---|---|---|
| 1 | 180 | 0.294 | 80.8 | 16.4 | 1.3 |
| 2 | 180 | 1.461 | 72.7 | 25.7 | 1.2 |
| 3 | 180 | 2.923 | 44.8 | 52.3 | 2.7 |
| 4 | 180 | 5.843 | 64.7 | 33.2 | 2.0 |

Example 4: Dosage Forms Comprising CRCRPS

Table 5 lists the components of exemplary dosage forms.

TABLE 5

Compositions of Dosage Forms

| Material | mg/dosage |
|---|---|
| CRCRPS | 285.7 |
| Ion exchange resin powder | 40 |
| Nasal irritant (sodium lauryl sulfate) | 30 |
| Super disintegrant | 100 |
| Magnesium stearate | 1.15 |

What is claimed is:

1. An extended release, abuse deterrent dosage form comprising a plurality of particles and at least one pharmaceutically acceptable excipient, wherein the plurality of particles consists of at least one active pharmaceutical ingredient (API) or a pharmaceutically acceptable salt thereof, at least one polyvinyl ester, at least one poly-N-vinylamide, at least one plasticizer, at least one optional lubricant, at least one optional polyalkylene oxide, and at least one optional wetting agent.

2. The extended release, abuse deterrent dosage form of claim 1, wherein the at least one API is oxycodone, oxymorphone, hydrocodone, hydromorphone, codeine, or morphine.

3. The extended release, abuse deterrent dosage form of claim 1, wherein the at least one polyvinyl ester is polyvinyl acetate.

4. The extended release, abuse deterrent dosage form of claim 1, wherein the at least one poly-N-vinylamide is polyvinylpyrrolidone.

5. The extended release, abuse deterrent dosage form of claim 1, wherein the at least one plasticizer is polyethylene glycol, propylene glycol, glycerin, polyethylene glycol monomethyl ether, sorbitol sorbitan solution, triethyl cellulose, dicarboxylic acid ester, acetyl tributyl citrate, acetyl triethyl citrate, castor oil, vegetable oil, diacetylated monoglyceride, dibutyl sebacate, diethyl phthalate, triacetin, tributyrin, tributyl citrate, triethyl citrate, polaxamer, or combination thereof.

6. The extended release, abuse deterrent dosage form of claim 1, wherein the at least one optional lubricant is magnesium stearate, calcium stearate, zinc stearate, colloidal silicon dioxide, hydrogenated vegetable oil, sterotex, polyoxyethylene monostearate, polyethylene glycol, sodium stearyl fumarate, sodium benzoate, sodium lauryl sulfate, magnesium lauryl sulfate, light mineral oil, or combination thereof.

7. The extended release, abuse deterrent dosage form of claim 1, wherein the at least one optional polyalkyene oxide is polyethylene oxide having an average molecular weight distribution from about 100,000 to about 7,000,000.

8. The extended release, abuse deterrent dosage form of claim 1, wherein the at least one optional wetting agent is polyoxyethylene glycol alkyl ether, polyoxyethylene glycol sorbitan alkyl ester, polyethylene glycol ester, sorbitan fatty acid ester, glyceryl fatty acid esters, polyethylene glycol, block co-polymer of polyethylene glycol and polypropylene glycol, polaxamer, polyoxyethylene fatty acid amide, polysorbate, ethoxylated aliphatic alcohol, alkylphenol, alkyl sulfate, alkyl sulfonate, alkyl benzene sulfonate, alpha sulfonyl fatty acid, alkyl phosphate, dioctyl sulfosuccinate, isethionate, alkyl ether sulfate, methyl sarcosine, alkyltrimethylammonium bromide, cetyltrimethylammonium bromide, benzalkonium chloride; benzethonium chloride, (3-((3-cholamidopropyl) dimethylammonio)-1-propanesulfonate (CHAPS), lecithin, cocoaminopropyl betaine, or combination thereof.

9. The extended release, abuse deterrent dosage form of claim 1, wherein the plurality of particles has an average particle size distribution from about 100 micrometers to about 1000 micrometers.

10. The extended release, abuse deterrent dosage form of claim 1, wherein the plurality of particles is resistant to crushing, grinding, milling, or pulverizing to form a powder comprising particles having an average diameter of less than about 10 micrometers.

11. The extended release, abuse deterrent dosage form of claim 1, wherein the plurality of particles releases the API over an extended period of time when the dosage form is crushed, broken, ground, milled, or pulverized.

12. The extended release, abuse deterrent dosage form of claim 1, wherein the dosage form is formulated for oral delivery.

13. The extended release, abuse deterrent dosage form of claim 12, wherein the dosage form is a tablet.

14. The extended release, abuse deterrent dosage form of claim 13, wherein the at least one pharmaceutically acceptable excipient is a binder, a filler, a super-disintegrant, a lubricant, an ion exchange resin powder, or a combination thereof.

15. The extended release, abuse deterrent dosage form of claim 13, wherein the tablet further comprises an aversive agent chosen from an irritant, a bittering agent, an emetic, a dye, or a combination thereof.

16. The extended release, abuse deterrent dosage form of claim 12, wherein the dosage form is a capsule.

17. The extended release, abuse deterrent dosage form of claim 16, wherein the at least one pharmaceutically acceptable excipient is a gelling polymer, a filler, an effervescent system, a glidant, an ion exchange resin powder, or a combination thereof.

18. The extended release, abuse deterrent dosage form of claim 16, wherein the capsule further comprises an aversive agent chosen from an irritant, a bittering agent, an emetic, a dye, or a combination thereof.

19. The extended release, abuse deterrent dosage form of claim 1, wherein the at least one polyvinyl ester is polyvinyl acetate; the at least one poly-N-vinylamide is polyvinylpyrrolidone; the at least one plasticizer is diethyl phthalate or a combination of diethyl phthalate and polyethylene glycol; the at least one optional polyalkylene oxide is polyethylene oxide; the at least one optional lubricant is present and is magnesium stearate, silicon dioxide, or a combination thereof; and the at least one optional wetting agent is present and is sodium lauryl sulfate.

20. The extended release, abuse deterrent dosage form of claim 19, wherein the at least one API is oxycodone, oxymorphone, hydrocodone, hydromorphone, codeine, or morphine.

* * * * *